(12) United States Patent
Kathe et al.

(10) Patent No.: US 8,236,567 B2
(45) Date of Patent: Aug. 7, 2012

(54) METHOD AND APPARATUS FOR AUTOMATED DETERMINING OF CHEMICAL OXYGEN DEMAND OF A LIQUID SAMPLE

(75) Inventors: Ulrich Kathe, Leonberg (DE); Kristoff Kley, Stuttgart (DE); Thomas Schipolowski, Stuttgart (DE); Lydia Hoppe, Ditzingen (DE)

(73) Assignee: Endress + Hauser Conducta Gesellshaft fur Mess-und Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 12/805,305

(22) Filed: Jul. 23, 2010

(65) Prior Publication Data

US 2011/0027893 A1 Feb. 3, 2011

(51) Int. Cl.
*G01N 33/18* (2006.01)
*G01N 33/00* (2006.01)
*G01N 31/00* (2006.01)

(52) U.S. Cl. ............... 436/62; 73/53.01; 73/61.41
(58) Field of Classification Search .............. 436/62; 73/53.01, 61.41
See application file for complete search history.

(56) References Cited

U.S. PATENT DOCUMENTS

| | | | | |
|---|---|---|---|---|
| 3,540,845 A | * | 11/1970 | Hickey et al. | 436/62 |
| 3,930,798 A | * | 1/1976 | Schierjott et al. | 436/62 |
| 2011/0042308 A1 | | 2/2011 | Krause | |

FOREIGN PATENT DOCUMENTS

| | | |
|---|---|---|
| DE | 195 45 130 C2 | 6/1997 |
| DE | 196 17 707 A1 | 11/1997 |
| DE | 103 60 066 A1 | 7/2005 |
| DE | 10 2008 021 190 A1 | 11/2009 |
| DE | 10 2008 021190 A1 | 11/2009 |

OTHER PUBLICATIONS

Wayne Boyles, "The Science of Chemical Oxygen Demand", Technical Information Series, Brooklet No. 9, 1997.
Berichterstatter: Hans Jurgen Busse, Chemische Werke Huls AG, pp. 17-25, 1975.
The English translation for Berichterstatter: Hans Jurgen Busse, Chemische Werke Huls AG (beginning on p. 22, and ending on p. 23, right column, last paragraph before Article 5.3 begins), 1975.

\* cited by examiner

*Primary Examiner* — Christine T Mui
(74) *Attorney, Agent, or Firm* — Bacon & Thomas, PLLC

(57) ABSTRACT

A method and apparatus for automated determining of the chemical oxygen demand of a liquid sample, comprising steps as follows: mixing the liquid sample with sulfuric acid; introducing a carrier gas, especially air, into the liquid sample-sulfuric acid mixture; adding an oxidizing agent to the liquid sample-sulfuric acid mixture to form a reaction mixture; heating (especially under reflux conditions) the reaction mixture at the boiling temperature of the reaction mixture for a predetermined time period; photometrically determining consumption of an oxidizing agent in the reaction mixture; and ascertaining therefrom the chemical oxygen demand of the liquid sample, wherein all steps are automatedly performed in an analytical system with the assistance of an evaluating and control unit.

24 Claims, 1 Drawing Sheet

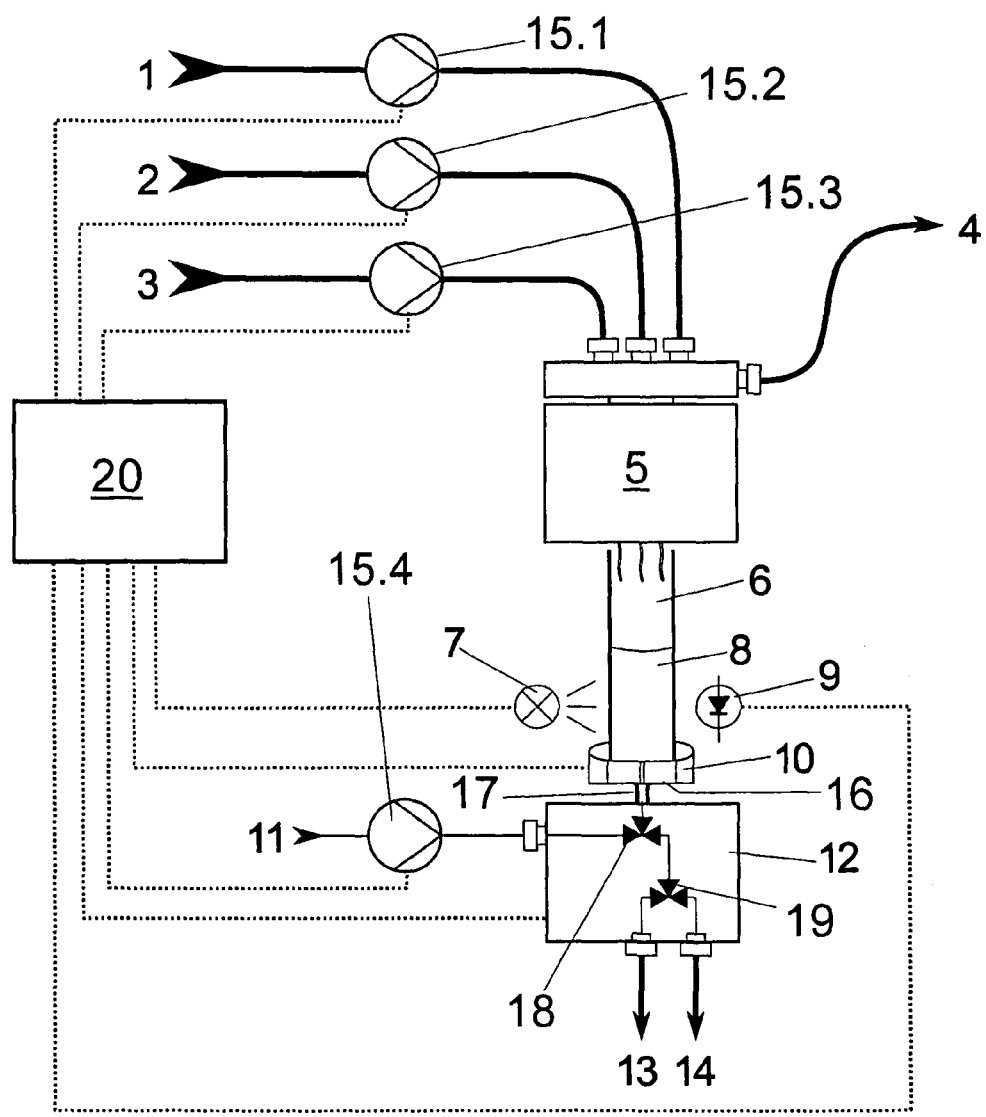

METHOD AND APPARATUS FOR AUTOMATED DETERMINING OF CHEMICAL OXYGEN DEMAND OF A LIQUID SAMPLE

TECHNICAL FIELD

The invention relates to a method for automated determining of the chemical oxygen demand of a liquid sample.

BACKGROUND DISCUSSION

Chemical oxygen demand (COD for short) is the amount (expressed as oxygen equivalent) of a chemical compound—usually a strong oxidizing agent, for example potassium permanganate or potassium dichromate—which is consumed by oxidizable ingredients contained in a certain volume of liquid sample under the reaction conditions of a prescribed method. The COD value is an important parameter for classification of the degree of fouling in flowing water, and in wastewater, and clarification, plants, especially as regards organic impurities.

The fundamental principle of most methods for determining chemical oxygen demand is that a sample is treated with a known excess of an oxidizing agent, and consumption of the oxidizing agent is then ascertained, for example, through back titration of the remainder which is not consumed. The amount of the oxidizing agent consumed is converted into the equivalent amount of oxygen.

In the state of the art, several methods are known for automatedly determining the COD value of a liquid sample. German patent application DE 103 60 066 A1 describes an automated method for photometric determining of the COD value of a liquid sample, in the case of which a cuvette containing the liquid sample and potassium dichromate (as digestion agent) is, during a digestion time, heated under pressure-tight closure to a temperature above the atmospheric boiling temperature of the reaction mixture; wherein to accelerate the reaction time, the cuvette is subjected to a pressure of 5 to 10 bar, so that the reaction mixture can be heated to a temperature of e.g. 175° C., which lies clearly above the boiling temperature at atmospheric pressure. At the same time, the absorbance of the reaction mixture is ascertained at least one fixed wavelength in the cuvette during the total digestion. The change in absorbance serves as a measure for the concentration change of the oxidizing agent in the reaction mixture.

Chloride ions present in the reaction mixture can disturb the ascertaining of the chemical oxygen demand according to this method. For this reason, mercury(II)-sulfate ($HgSO_4$) is added to the reaction mixture to mask the chloride-ions in the liquid sample. $HgSO_4$ proves most effective when it is present in a quantity ten times that of chloride content. Mercury(II) salts are, however, highly poisonous, so a reaction mixture treated in such a manner cannot be returned directly to the water system. Instead, it must be disposed of in a complicated manner at high cost. Furthermore, the relatively high amounts of mercury(II)-salt which are required over the duration of the operation of the automatic analytical system pose a danger to operating personnel and to the environment. Consequently, ISO 6060, for example, allows a chloride content of only up to 1000 mg/l in the sample.

A method is known from the article "Instrumentelle Bestimmung der organischen Stoffe in Wässern" (Instrumental Determining of Organic Materials in Water) in the Zeitschrift für Wasser-und Abwasser-Forschung (Journal of Water, and Wastewater, Research), Vol. 9, No. 1/76, pages 17 to 25, in which the chloride present in the liquid sample is not masked by mercury(II) salts, but instead separated from the liquid sample before the addition of an oxidizing agent. In this regard, before the addition of the oxidizing agent, the sample is so strongly acidified using pure, concentrated sulfuric acid at a proportion 1:1, that the chloride can be completely removed from the reaction mixture as hydrochloric acid, for example by gas purging. The described method functions continuously. In such a case, the sample is first brought together with the concentrated sulfuric acid and led through a degassing tube. In the degassing tube, air is blown through the sample, moving in the same direction as the sample and taking the separated hydrochloric acid with it. Half of the acidified and degassed sample is combined with the oxidizing reagent—a solution of potassium dichromate and silver sulfate in concentrated sulfuric acid at a proportion of 1:1—and led through a digesting unit, in which the organic materials present in the reaction mixture are oxidized. The digesting unit is composed of a long helical tube, which is heated by means of a thermostat. Half of the reaction mixture is then once again removed, and the excess potassium dichromate not consumed during the oxidation of the organic materials is ascertained. For this purpose, the remaining solution is combined with a standard solution of iron(II)- and iron(III)-sulfate, and led to a measuring unit via a mixing vessel. Via the measuring unit, the change in redox potential of the standard solution is measured, which comes about through oxidation of iron(II) ions into iron(III) ions by the potassium dichromate not consumed.

This method is quite complicated, and the corresponding automatic analytical apparatus is high in maintenance and susceptible to defects. For example, a series of liquid conducting lines between the reagent containers, the degassing tube, the digesting unit and the measuring unit are necessary. Such hose lines must regularly be changed, which requires a high maintenance effort. Added to this is the fact that, due to the complexity of the overall construction, it can easily happen that connections for the liquid transport lines are accidentally switched. Furthermore, the functional units of the analytical apparatus are complex and delicate in their construction. An example of this is the helical tube serving as the digesting unit; such a component is expensive to manufacture, relatively difficult to clean and susceptible to defects. The same is true for the degassing tube. This method and the corresponding apparatus are therefore rather poorly suited for use in process analytics.

SUMMARY OF THE INVENTION

It is, consequently, an object of the invention to provide a method and an apparatus for automated determining of the chemical oxygen demand of a liquid sample, which overcomes the disadvantages of the state of the art. In particular, the amount of dangerous (especially poisonous) process waste should, on one hand, be reduced, and, on the other hand, the method and the apparatus should be suitable for use in process analytics, i.e., the method should especially be put into practice through a robust, low-maintenance apparatus, which is not very susceptible to defects.

This object is achieved by a method for determining chemical oxygen demand of a liquid sample, comprising steps as follows:
  mixing the liquid sample with sulfuric acid;
  introducing a carrier gas (especially air) into the liquid sample-sulfuric acid mixture, and extracting the carrier gas from the liquid sample;
  adding an oxidizing agent to the liquid sample-sulfuric acid mixture to form a reaction mixture;

heating (especially under reflux conditions) the reaction mixture at the boiling temperature of the reaction mixture for a predetermined length of time;

photometrically determining consumption of the oxidizing agent in the reaction mixture; and ascertaining therefrom the chemical oxygen demand of the liquid sample;

wherein all steps are automatedly performed in an analytical system with the assistance of an evaluating and control unit.

By mixing the liquid sample with sulfuric acid, hydrochloric acid gas (HCl) forms from chlorides present in the liquid sample. This can be purged by the introduction of a carrier gas into the liquid sample-sulfuric acid mixture, in that the carrier gas is enriched with HCl when it leaves the liquid sample. In this way, disturbing chloride ions can be completely removed from the liquid sample, so that the addition of mercury(II) salts in the oxidation of organic substances contained in the liquid sample can be omitted, without, in such case, damaging the accuracy of the COD determination. By photometrically determining the consumption of the oxidizing agent, the analytical system can be constructed in a significantly simpler manner than the analytical system for electrochemically determining the consumption of an oxidizing agent, as described in the article cited above, because, for photometrically determining the consumption of the oxidizing agent, only one or more light sources of defined wavelength, one or more photodetectors and corresponding evaluating electronics are required.

The steps of the method are, preferably, executed one after the other. It is, however, also possible to perform the photometric determining of the consumption of the oxidizing agent during the heating of the reaction mixture, and thus to obtain, for example, information concerning the decrease in the chromium(VI) concentration of the reaction mixture during the digestion (i.e. during the heating of the reaction mixture).

When the parameter to be determined is the COD value of the liquid sample, potassium dichromate ($K_2Cr_2O_7$) is preferably used as oxidizing agent, wherein, especially, a potassium dichromate solution in 10 to 30% sulfuric acid having a potassium dichromate concentration of 3 to 120 g/l is added to the reaction mixture.

In order to configure the automatic analytical apparatus in an especially simple and compact manner, the mixing of the liquid sample with sulfuric acid, the addition of a carrier gas to the liquid sample-sulfuric acid mixture, the addition of an oxidizing agent, the heating of the reaction mixture and the photometric determining of the consumption of the oxidizing agent can be performed in a single digestion vessel. The digestion vessel can, for example, essentially have the shape of a cylinder, especially a cylinder standing upright.

It is also possible to perform the individual steps of the method in separate vessels. Thus, for example, the mixing of the liquid sample with sulfuric acid and the addition of a carrier gas into the liquid sample-sulfuric acid mixture can be performed in a purging vessel, and the liquid sample-sulfuric acid mixture or an aliquot can then be transferred to a digestion vessel, in which the addition of oxidizing agents and the heating of the reaction mixture is performed. Subsequently, the reaction mixture or an aliquot can be transferred to a cuvette, in order to photometrically determine the consumption of the oxidizing agent. Transfer between the purging vessel, the digestion vessel and the cuvette can occur via liquid transport lines with the assistance of a dosing, metering and supply unit (for example a pump). Alternatively, the mixing of the liquid sample with sulfuric acid and the addition of a carrier gas to the liquid sample-sulfuric acid mixture can also be performed in one and the same purging vessel, and the liquid sample-sulfuric acid mixture or an aliquot can then be transferred to a digestion vessel, in which the addition of the oxidizing agent and the heating of the reaction mixture, as well as the photometrically determining consumption of the oxidizing agent, is performed. For this purpose, the digestion vessel can have optical windows or a wall which is transmissive for the photometric measuring wavelength. Alternatively, the mixing of the liquid sample with sulfuric acid could also be performed in a mixing vessel, and the liquid sample-sulfuric acid mixture or an aliquot can then be transferred to a purging vessel, in which the addition of a carrier gas is performed; the liquid sample or an aliquot then being transferred to a digestion vessel, in which the addition of an oxidizing agent and the heating of the reaction mixture is performed; and the reaction mixture or an aliquot then being transferred to a cuvette, in order to photometrically determine the consumption of the oxidizing agent.

For extracting the HCl gas from the liquid sample-sulfuric acid mixture, it can be advantageous to heat the liquid sample-sulfuric acid mixture to a temperature in the range of 40 to 50° C. during introduction of the carrier gas. The carrier gas is preferably introduced into the liquid mixture through a gas inlet, and removed again from the purging vessel (especially from the digestion vessel) through a gas outlet, wherein the carrier gas is cooled in the region the gas outlet. In this way, loss of easily volatile organic compounds from the liquid sample along with the carrier gas containing the hydrochloric acid is lessened.

A catalyst (for example, silver sulfate) can additionally be added to the reaction mixture to accelerate the reaction with the oxidizing agent. The catalyst is preferably added to the reaction mixture as catalyst solution, for example, as a sulfuric acid-silver sulfate solution.

The predetermined time period, over which the reaction mixture is heated under reflux, can be between 15 and 120 minutes.

When the oxidizing agent used (e.g. potassium dichromate) is not completely converted by the liquid sample, a certain portion of the oxidizing agent (e.g. chromium(VI)) remains in the reaction mixture. In an advantageous variant of the method, after performing the analytical determining of the COD content, the reaction mixture is transferred to a waste vessel, which contains a reducing agent able to reduce the oxidizing agent still contained in the reaction mixture. In the case of potassium dichromate as oxidizing agent, the chromium(VI) is, in this way, reduced to the essentially less poisonous chromium(III). Sucrose, for example, can be used as reducing agent. The process waste occurring in the previously described analytical method then contains no substances which strongly burden the environment, especially no mercury(II) and no chromium(VI).

The steps:

mixing the liquid sample with sulfuric acid;

introducing a carrier gas, especially air, into the liquid sample-sulfuric acid mixture;

adding an oxidizing agent to the liquid sample-sulfuric acid mixture to form a reaction mixture;

heating (especially under reflux conditions) the reaction mixture at the boiling temperature of the reaction mixture for a predetermined time period; and photometrically determining the consumption of the oxidizing agent in the reaction mixture and ascertaining therefrom the chemical oxygen demand of the liquid sample;

form a measuring cycle. After a predetermined number of measuring cycles, especially after each measuring cycle, those parts of the analytical apparatus which come into contact with the liquid sample and/or with the reaction mixture—especially the liquid transport lines and/or the digestion vessel, or, as the case may be, other, vessels present—are rinsed with a cleaning solution.

After a predetermined number of measuring cycles, especially after each measuring cycle, one or more photometric calibration measurements for calibrating the photometer are performed with one or more standard solutions. Preferably, the cleaning solutions and calibration solutions are automatedly introduced into the analytical apparatus via a pump and supply system.

The above-named object is furthermore achieved by an apparatus for automatedly determining the chemical oxygen demand of a liquid sample, wherein the apparatus includes:

a mixing and purging unit, which has liquid supply lines for liquid sample and for sulfuric acid, as well as a gas inlet and a gas outlet for a carrier gas;

a digesting unit, which has a liquid supply line for adding an oxidizing agent to the liquid sample for forming a reaction mixture, as well as a heating means for heating the reaction mixture and a cooling apparatus;

a photometric unit with a cuvette for accommodating the reaction mixture and a light source for irradiating the reaction mixture accommodated in the cuvette along a measuring path; and with a light receiver for registering intensity of light emitted from the light source after traveling the measuring path;

a supply and dosing system for conveying and dosing liquid sample, sulfuric acid and carrier gas into the mixing and purging system, and for conveying and dosing oxidizing agent into the digestion system; and an evaluating and control unit for controlling the supply and dosing system, the heating means and the photometer, as well as for determining chemical oxygen demand of the liquid sample from a signal of the photometer.

The measuring path extends between the light source and light receiver, through the reaction mixture. The light receiver thus receives the light from the light source weakened in its intensity due to absorption by the reaction mixture. The light source and light receiver can especially be arranged opposite each other on opposing sides of the cuvette.

The apparatus can especially be embodied in a compact and robust manner by providing it with a single digestion vessel, into which liquid supply lines for liquid sample, sulfuric acid and oxidizing agent open; wherein the gas inlet for the carrier gas is arranged in a lower region of the digestion vessel, and the gas outlet is arranged in an upper region of the digestion vessel; and wherein the digestion vessel has a wall which is transparent for a measuring wavelength range of the photometer, and the light source and the light receiver of the photometer are arranged in the region of such transparent wall. The digestion vessel is, in this case, simultaneously a component of the mixing and purging unit, of the digesting unit and of the photometric unit. The digestion vessel, in contrast to the above described helical tube known in the state of the art, can be constructed in a considerably simpler manner. It can, for example, be embodied as an essentially cylindrical glass vessel, and thus have a vessel wall which is transmissive for the photometric measuring radiation.

The mixing and purging unit, the digesting unit and the photometric unit can also comprise their own respective vessels. The sample liquid (or the reaction mixture) can be transported from one vessel to another via liquid transport lines. For effecting the liquid transport between the vessels, the supply and dosing system can be used.

For the oxidizing agent, potassium dichromate can be used, which is provided in an aqueous potassium dichromate solution—especially a potassium dichromate solution in 10 to 30% sulfuric acid—having a potassium dichromate-concentration of 3 to 120 g/l. The heating means can be arranged in a lower region of the digestion vessel, while a cooling apparatus can be arranged in an upper region of the digestion vessel. This arrangement is, for one, advantageous for purging hydrochloric acid gas from the liquid mixture containing the liquid sample and concentrated sulfuric acid. In such a case, the liquid mixture can, with the assistance of the heating means, be heated in order to accelerate the loss of HCl. In order to, in such case, prevent simultaneous loss of easily volatile organic substances from the liquid sample, the cooling apparatus can be utilized, which is arranged in the upper region, i.e. also arranged in the region of the gas outlet of the digestion vessel. The same arrangement of the heating means in the lower region of the digestion vessel and the cooling apparatus in the upper region of the digestion vessel can be utilized to boil the reaction mixture combined with the oxidizing agent under reflux, and thus to achieve as complete as possible conversion of the organic substances in the liquid sample. The cooling effect of the cooling apparatus is preferably achieved through a thermoelectric element, e.g. a Peltier-element. This has the advantage that only electrical connections must be provided for the cooling. Connections for cooling water or other cooling means can thereby be omitted.

The analytical apparatus can comprise an additional liquid supply line to the digestion vessel for a catalyst solution. Especially a sulfuric acid/silver sulfate solution is a preferred catalyst.

The digestion vessel—or, in the case of the photometric determining of the consumption of the oxidizing agent occurring in a separate cuvette which is connected with the digestion vessel via liquid transport lines, the cuvette—can have a liquid discharge, via which, after the COD value is determined, the used reaction mixture (containing the liquid sample, sulfuric acid, chromium(VI) and chromium(III)) can be discharged from the analytical apparatus. The liquid discharge preferably opens into a waste vessel, in which a reducing agent (e.g. sucrose) is present, which is able to reduce the oxidizing agent (especially chromium(VI)) still present in the reaction mixture. In this way, it is achieved, that the process waste of the analytical apparatus, which is to be disposed of, exclusively contains essentially nonpoisonous substances.

A second waste vessel can also be provided (which is isolated from the waste vessel for chromium-containing waste water) into which used calibration and rinsing liquids can be conducted.

BRIEF DESCRIPTION OF THE DRAWING

In the following, the invention will now be explained in greater detail on the basis of the illustrated example of an embodiment in the drawing, the sole FIGURE of which shows as follows:

FIG. 1 is an apparatus for determining the COD value of a liquid sample.

DETAILED DISCUSSION IN CONJUNCTION WITH THE DRAWING

FIG. 1 schematically illustrates an apparatus for determining the COD value of a liquid sample, especially a wastewater sample. The analytical apparatus possesses a digestion vessel 6 (made of glass), which has the shape of a cylinder standing upright-. For conveying the liquid sample, a liquid supply line 1 is provided, which leads from a sample supply (not shown) to the digestion vessel 6. For conveying the sulfuric acid, a liquid supply line 2 is present, which likewise leads from a sulfuric acid supply vessel (not shown) to the digestion vessel 6. A third liquid supply line 3 is provided for delivery of an oxidizing agent, for example, a potassium dichromate solution. A supply and dosing system 15.1, 15.2 and 15.3 serves to supply the liquid sample, the sulfuric acid and the oxidizing agent via the liquid supply lines 1, 2 and 3. For the supply and dosing systems 15.1, 15.2 and 15.3, peristaltic pumps, for example, which act upon the liquid supply lines 1, 2 and 3 according to the peristaltic-principle, are a possibility. An individual peristaltic pump, which acts on all three liquid supply lines 1, 2 and 3, can also be provided.

The digestion vessel includes in a lower region—in the example shown, on the vessel's base 16—a liquid and gas connection 17. This is connected with a three-way valve 18. The three-way valve 18 connects the liquid and gas connection 17, with, on the one hand, an additional three-way valve 19 and, on the other hand, with a gas supply line 11. Via the gas supply line 11 and the three-way valve 18, a carrier gas (for example air), can enter into the digestion vessel 6. For fine distribution of the carrier gas in the liquid mixture within the digestion vessel, a nozzle or a fritted glass (not shown) can be provided in the end region of the gas supply line 11. For supplying the carrier gas to the digestion vessel 6, a dosing, metering and supply unit 15.4 is used, which can be embodied as a pump. For delivering the carrier gas, a gas cylinder with a regulatable valve can also be provided as the dosing, metering and supply unit 15.4. The carrier gas brought into the digestion vessel 6 can be removed via a gas outlet 4 in the upper region of the digestion vessel 7. In the upper region of the digestion vessel 6—and thus in the region of the gas outlet 4—a cooling apparatus 5 is located. This preferably includes a thermoelectric element, for example a Peltier-element, which causes the cooling effect of the cooling apparatus 5. Cooling can also be achieved by means of an air or liquid cooling or a heat pipe. In the lower region of the digestion vessel 6—in which, during operation of the apparatus, the reaction mixture 8 is also present—a heating apparatus 10 is arranged.

The three-way valve 18, which is connected with the liquid and gas connection 17 of the digestion vessel 6, is furthermore connected with an additional three-way valve 19. Via a first connection, this second valve is connected with a waste vessel 13 for used reaction mixture 8 (chromium-containing waste water). Via a second connection, the three-way valve 19 is connected with an additional waste vessel 14 for rinsing and calibration liquids. Both three-way valves 18 and 19 are arranged in a valve block 12.

The dosing, metering and supply systems 15.1, 15.2, 15.3, 15.4, the heating apparatus 10, the cooling apparatus 5 and the valve block 12 are connected with an evaluating and control unit 20, which includes a data processing system (for example, a microprocessor). Preferably, the evaluating and control unit 20 furthermore includes a display unit and an input apparatus for use by a service person.

The analytical apparatus furthermore includes a photometer having a light source 7 and a light receiver 9. The light source 7 can, for example, be an LED or a flash lamp. In the latter case, by means of a grating (as a dispersing element), a measuring wavelength of the light source 7 can be selected, with which the reaction mixture 8 should be irradiated; or, alternatively, the sample is irradiated with the total bandwidth of the radiation emitted by the light source 7, and a wavelength is selected, which is registered by the light receiver 9.

The light receiver 9 includes at least one photodiode, preferably a photodiode array. The light of the light source 7 irradiates the digestion vessel 6 (and the reaction mixture 8 contained by the digestion vessel 6), and hits the light receiver 9. For this purpose, the digestion vessel 6 can—as illustrated in the example here—be produced from a material transparent for the wavelength, for example glass. The vessel can also be made from a material not transparent for the wavelength of the light source, and simply have windows, through which radiation emitted from the light source 7 can pass along the measuring path, through the reaction mixture 8, to the light receiver 9. The measurement signal—which is produced by the light receiver 9 as a function of the light intensity hitting the light receiver 9—is fed to a signal processing unit, which ascertains from the receiver signal an absorbance of the reaction mixture 8. Preferably, the signal processing unit is part of the evaluating and control unit 20. The data processing unit of the evaluating and control unit 20 ascertains the consumption of the oxidizing agent from the absorbance of the reaction mixture 8.

The process sequence for photometrically determining the COD value of a liquid sample by means of the automatic analytical apparatus illustrated in FIG. 1 is, for example, as follows:

First, a liquid sample is metered into the digestion vessel 6 via the liquid supply line 1 by means of the dosing, metering and supply system 15.1. The volume of the liquid sample can be between 0.1 and 20 ml, preferably between 0.5 and 5 ml. Concentrated sulfuric acid is added to the liquid sample in the digestion vessel 6 via the liquid supply line 2 by means of the dosing, metering- and supply system 15.2, so that a liquid mixture concentration of more than 50 volume % sulfuric acid is obtained. In such a case, hydrochloric acid gas (HCl) forms, which is then present in dissolved form in the liquid mixture containing the liquid sample and sulfuric acid.

In an additional step, a carrier gas for purging the hydrochloric acid gas from the liquid mixture is introduced via the gas supply line 11. The throughput of the carrier gas is set to 20 to 2000 ml/min, preferably between 100 and 500 ml/min. The introduction of the gas can occur via a nozzle or fritted glass (not shown), so that the introduced gas is finely distributed over a large part of the liquid mixture contained in the digestion vessel 6. For accelerating the ejection of the HCl gas, the temperature of the liquid mixture can, by means of the heating apparatus 10, be moderately increased, preferably to a temperature between 40 and 50° C. In order to prevent easily volatile organic substances in the liquid sample from being lost from the digestion vessel along with the carrier gas by the process of heating and purging, the carrier gas is cooled in the region of the gas outlet 4 by means of the cooling apparatus 5. Depending on the chloride content present in the liquid sample, the purging process is finished after about 2 to 15 minutes.

In a next step, a potassium dichromate solution is added to the now degassed and chloride-free liquid sample-sulfuric acid mixture via the liquid supply line 3 by means of the dosing, metering- and supply system 15.3. The potassium dichromate-solution is preferably produced by dissolving 3 to 120 g potassium dichromate per liter of 10 to 30% sulfuric acid. The solution can additionally contain silver sulfate. A sulfuric acid-silver sulfate solution can also be introduced into the digestion vessel 6, especially via an additional liquid supply line with its own dosing, metering- and supply system (not shown in FIG. 1). The reaction mixture 8 thus formed is, by means of the heating apparatus 10, heated at atmospheric pressure to boiling temperature (i.e. about 150° C.), and, with the assistance the cooling apparatus 5, is boiled under reflux conditions for a predetermined digestion time. Depending on the type of sample, the digestion time ranges from 15 to 120 minutes.

Once the predetermined digestion time has elapsed, the potassium dichromate content remaining in the reaction mixture 8 and/or the amount of potassium dichromate consumed during the oxidation of the oxidizable substances (especially organic substances) contained in the liquid sample is ascertained by means of the photometer having the light source 7 and the light receiver 9. For this purpose, either the amount of chromium(VI) remaining in the reaction mixture 8 or the amount of chromium(III) arising during the oxidation of the oxidizable substances contained in the liquid sample is ascertained. Chromium(VI) has an absorption maximum at about 430 nm. A suitable wavelength for determining the chromium (VI) content of the reaction mixture correspondingly lies at 390 to 490 nm. Chromium(III) has an absorption maximum at about 610 nm. A correspondingly suitable wavelength for determining the chromium(III) content of the reaction mixture thus lies between 560 and 660 nm. The wavelength emitted by the light source 7 is to be accordingly selected depending on whether chromium(VI) or chromium(III) can be ascertained in the reaction mixture.

From the intensity (detected by the light receiver 9) of the radiation transmitted by the light source 7 through the reaction mixture 8, the evaluating and control unit 20 ascertains (according to a method known in the state of the art) the absorbance of the reaction mixture 8 and/or the concentration of chromium(III) or chromium(VI) in the reaction mixture 8, and from this ascertains the consumption of chromium(VI) on the basis of the potassium dichromate concentration known to have originally been present in the sample. This consumption is converted into oxygen equivalents—i.e. into a COD value—by the control unit 20.

After the COD value is determined, the digestion vessel 6 is emptied. The emptying of the digestion vessel 6 occurs via the liquid discharge 17. In such case, the control unit sets the two three-way valves 18 and 19 in such a way, that the used reaction mixture 8, which still contains chromium(III) and chromium(VI), arrives in the waste vessel 13 for chromium-containing waste water. In the waste vessel 13, a reducing agent—for example, sucrose—can be provided, by which the chromium(VI) still in the reaction mixture is reduced to the essentially less dangerous chromium(III).

The sequence for COD determining forms a measuring cycle. After completion of one or more measuring cycles, the analytical apparatus can be cleaned. For this purpose, a cleaning liquid is, for example, introduced into the analytical apparatus via the liquid supply line 1, through which the liquid sample is introduced during COD determining. This cleaning liquid rinses the digestion vessel 6 and the liquid discharge 17. The rinse water can, by means of the three-way valve 19, be collected in a second waste water vessel 14, which is separate from the waste vessel 13 for chromium-containing waste water. Similarly, instead of the rinsing liquid, a standard solution can also be brought into the digestion vessel, in order to thereby perform a calibration of the photometer.

The invention claimed is:
1. A method for the automated determining of the chemical oxygen demand of a liquid sample, comprising the steps:
mixing the liquid sample with sulfuric acid;
introducing a carrier gas, especially air, into the liquid sample-sulfuric acid mixture and extracting the carrier gas from the liquid sample-sulfuric acid mixture;
adding an oxidizing agent to the liquid sample-sulfuric acid mixture to form a reaction mixture;
heating the reaction mixture at the boiling temperature of the reaction mixture for a predetermined time period;
photometrically determining consumption of said oxidizing agent in the reaction mixture including: irradiating the reaction mixture with light of a light source passing along a measuring path through the reaction mixture to a light receiver; ascertaining from the corresponding light receiver signal an absorbance of the reaction mixture; and ascertaining therefrom the consumption of said oxidizing agent in the reaction mixture; and
ascertaining the chemical oxygen demand of the liquid sample from the determined consumption of said oxidizing agent in the reaction mixture, wherein:
all steps are automatedly performed in an analytical system with the assistance of an evaluating and control unit.
2. The method as claimed in claim 1, wherein:
potassium dichromate ($K_2Cr_2O_7$) is used as an oxidizing agent.
3. The method as claimed in claim 1, wherein:
the mixing of the liquid sample with sulfuric acid, the introducing of a carrier gas into the liquid sample-sulfuric acid mixture, the adding of the oxidizing agent, the heating of the reaction mixture and the photometric determining of the consumption of the oxidizing agent is performed in a digestion vessel.
4. The method as claimed in claim 1, wherein:
during the introducing of the carrier gas, the liquid sample-sulfuric acid mixture is heated to 40 to 50° C.
5. The method as claimed in claim 1, wherein:
the carrier gas is introduced into the liquid sample-sulfuric acid mixture through a gas inlet, and is removed through a gas outlet, wherein the carrier gas is cooled in the region of the gas outlet.
6. The method as claimed in claim 1, wherein:
a catalyst is additionally added to the reaction mixture.
7. The method as claimed in claim 1, wherein:
said heating of the reaction mixture is performed under reflux conditions, especially for a time period between 15 and 120 minutes.
8. The method as claimed in claim 1, wherein:
after photometric determining of the consumption of the oxidizing agent, the reaction mixture is transferred to a waste vessel, which already contains a reducing agent, which is able to reduce the oxidizing agent still contained in the reaction mixture.
9. The method as claimed in claim 1, wherein a measuring cycle comprises the steps of: mixing the liquid sample with sulfuric acid; introducing a carrier gas into the liquid sample-sulfuric acid mixture; adding an oxidizing agent to the liquid sample-sulfuric acid mixture to form a reaction mixture; heating the reaction mixture at the boiling temperature of the reaction mixture for a predetermined time period; photometrically determining consumption of oxidizing agent in the reaction mixture; and ascertaining therefrom the chemical oxygen demand of the liquid sample
said measuring cycle is performed repeatedly; and
after a predetermined number of measuring cycles, those parts of the analytical system which come in contact with the liquid sample and/or the reaction mixture are rinsed with a cleaning solution.
10. The method as claimed in claim 1, wherein a measuring cycle comprises the steps of:
mixing the liquid sample with sulfuric acid; introducing a carrier gas into the liquid sample-sulfuric acid mixture; adding an oxidizing agent to the liquid sample-sulfuric acid mixture to form a reaction mixture; heating the reaction mixture at the boiling temperature of the reac- tion mixture for a predetermined time period; photometrically determining the consumption of the oxidizing agent in the reaction mixture and ascertaining therefrom the chemical oxygen demand of the liquid sample said measuring cycle is performed repeatedly; and after a predetermined number of measuring cycles, one or more photometric calibration measurements are performed with one or more standard solutions.

11. A method for the automated determining of the chemical oxygen demand of a liquid sample, comprising the steps:

mixing the liquid sample with sulfuric acid;

introducing a carrier gas, especially air, into the liquid sample-sulfuric acid mixture, and extracting the carrier gas from the liquid sample-sulfuric acid mixture and heating the liquid sample-sulfuric acid mixture to 40 to 50° C. during the introducing and extracting of the carrier gas;

adding an oxidizing agent to the liquid sample-sulfuric acid mixture to form a reaction mixture;

heating the reaction mixture at the boiling temperature of the reaction mixture for a predetermined time period;

photometrically determining consumption of said oxidizing agent in the reaction mixture; and ascertaining therefrom the chemical oxygen demand of the liquid sample, wherein:

all steps are automatedly performed in an analytical system with the assistance of an evaluation and control unit.

12. The method as claimed in claim 11, wherein:

the carrier gas is introduced into the liquid sample-sulfuric acid mixture through a gas inlet, and is removed through a gas outlet, wherein the carrier gas is cooled in the region of the gas outlet.

13. The method as claimed in claim 12, wherein:

said heating of the reaction mixture is performed under reflux conditions, especially for a time period between 15 and 120 minutes.

14. The method as claimed in claim 13, wherein said steps of: introducing a carrier gas into the liquid sample-sulfuric acid mixture and extracting the carrier gas from the liquid sample-sulfuric acid mixture and heating the liquid sample-sulfuric acid mixture to 40 to 50° C. during the introducing of the carrier gas; adding an oxidizing agent to the liquid sample-sulfuric acid mixture to form a reaction mixture; and heating the reaction mixture at the boiling temperature of the reaction mixture for a predetermined time period; are performed in a digestion vessel, said digestion vessel comprising a gas inlet being arranged in a lower region of said digestion vessel and a gas outlet being arranged in an upper region of said digestion vessel; and heating means being arranged in a lower region of said digestion vessel and a cooling apparatus being arranged in an upper region of said digestion vessel;

and wherein said heating means and said cooling apparatus are utilized both for preventing loss of easily volatile organic substances from the liquid sample-sulfuric acid mixture during the introducing and extracting of said carrier gas and for performing said heating of the reaction mixture under reflux conditions.

15. The method as claimed in claim 11, wherein:

after photometric determining of the consumption of the oxidizing agent, the reaction mixture is transferred to a waste vessel, which already contains a reducing agent, which is able to reduce the oxidizing agent still contained in the reaction mixture.

16. A method for the automated determining of the chemical oxygen demand of a liquid sample, comprising the steps:

mixing the liquid sample with sulfuric acid;

introducing a carrier gas, especially air, into the liquid sample-sulfuric acid mixture and extracting the carrier gas from the liquid sample-sulfuric acid mixture;

adding an oxidizing agent to the liquid sample-sulfuric acid mixture to form a reaction mixture;

heating the reaction mixture at the boiling temperature of the reaction mixture for a predetermined time period;

photometrically determining consumption of said oxidizing agent in the reaction mixture;

ascertaining therefrom the chemical oxygen demand of the liquid sample; and after photometrically determining said consumption of said oxidizing agent transferring the reaction mixture to a waste vessel, which already contains a reducing agent, which is able to reduce the oxidizing agent still contained in the reaction mixture; wherein:

all steps are automatedly performed in an analytical system with the assistance of an evaluation and control unit.

17. The method as claimed in claim 16, wherein:

potassium dichromate ($K_2Cr_2O_7$) is used as an oxidizing agent and sucrose is used as a reducing agent.

18. A method for the automated determining of the chemical oxygen demand of a liquid sample, comprising the steps:

mixing the liquid sample with sulfuric acid;

introducing a carrier gas, especially air, into the liquid sample-sulfuric acid mixture and extracting the carrier gas from the liquid sample-sulfuric acid mixture;

adding an oxidizing agent to the liquid sample-sulfuric acid mixture to form a reaction mixture;

heating the reaction mixture at the boiling temperature of the reaction mixture for a predetermined time period;

photometrically determining consumption of an said oxidizing agent in the reaction mixture; and ascertaining therefrom the chemical oxygen demand of the liquid sample, wherein:

all steps are automatedly performed in an analytical system with the assistance of an evaluation and control unit, wherein all steps of: mixing the liquid sample with sulfuric acid; introducing of a carrier gas into the liquid sample-sulfuric acid mixture and extracting the carrier gas from the liquid sample-sulfuric acid mixture; adding of the oxidizing agent; heating of the reaction mixture; and photometrically determining the consumption of the oxidizing agent; are performed in a digestion vessel.

19. The method as claimed in claim 18, wherein:

said digestion vessel comprising a gas inlet being arranged in a lower region of said digestion vessel and a gas outlet being arranged in an upper region of said digestion vessel.

20. The method as claimed in claim 19, wherein:

during the introducing and extracting of the carrier gas the liquid sample-sulfuric acid mixture is heated to 40 to 50° C. with the assistance of heating means being arranged in a lower region of said digestion vessel.

21. The method as claimed in claim 20, wherein:

the carrier gas is cooled in the region of said gas outlet with the assistance of a cooling apparatus being arranged in an upper region of said digestion vessel.

22. The method as claimed in claim 21, wherein:

said heating of the reaction mixture is performed under reflux conditions, especially for a time period between 15 and 120 minutes, with the assistance of said heating means and said cooling apparatus.

23. The method as claimed in claim 2, wherein:
a potassium dichromate solution in 10 to 30% sulfuric acid with a potassium dichromate concentration of 3 to 120 g/l is added to the reaction mixture.

24. The method as claimed in claim 2, wherein:
In order to photometrically determine the consumption of said oxidizing agent in the reaction mixture the amount of chromium (V) remaining in the reaction mixture is ascertained using a wavelength between 390 to 490 nm and/or the amount of chromium (III) present in the reaction mixture is ascertained using a wavelength between 560 and 660 nm.

* * * * *